| United States Patent [19] | [11] Patent Number: 4,880,601 |
| --- | --- |
| Andermann et al. | [45] Date of Patent: Nov. 14, 1989 |

[54] HYDROGEN PEROXIDE DISINFECTING SYSTEM FOR CONTACT LENSES

[75] Inventors: Guy Andermann, Strasbourg; Joseph Spittler, Kayersberg; Patricia Zilliox, Strasbourg; Dominique Mergel, Sigolsheim, all of France

[73] Assignee: Laboratoires, P.O.S., Kayserberg, France

[21] Appl. No.: 781,286

[22] Filed: Sep. 27, 1985

[51] Int. Cl.$^4$ .................................................. A61L 2/16
[52] U.S. Cl. ........................................ 422/28; 422/30; 422/292; 424/616; 514/840
[58] Field of Search ............................ 422/28, 292, 30; 514/840; 424/130

[56] References Cited

U.S. PATENT DOCUMENTS

| | | |
| --- | --- | --- |
| 3,912,451 | 10/1975 | Gaglia, Jr. . |
| 4,521,375 | 6/1985 | Houlsby .................................. 422/29 |
| 4,568,517 | 2/1986 | Kaspar et al. ......................... 422/30 |
| 4,812,173 | 3/1989 | Tsao et al. .............................. 134/27 |

OTHER PUBLICATIONS

Gasset et al., "Hydrogen Peroxide Sterilization of Hydrophilic Contact Lenses", *Arch Ophthalmol.*, vol. 93, pp. 412–415, Jun. (1975).

*Primary Examiner*—Barry S. Richman
*Assistant Examiner*—Jill Johnston
*Attorney, Agent, or Firm*—James A. Arno; Gregg C. Brown

[57] ABSTRACT

A system and method for disinfecting contact lenses with a stabilized hydrogen peroxide solution and a separate neutralizing solution are described. Sodium stannate (a.k.a. sodium tin oxide) is utilized to stabilize the hydrogen peroxide, and sodium thiosulfate is utilized to neutralize the hydrogen peroxide. In addition to sodium thiosulfate, the neutralizing solution also contains a complexing agent capable of sequestering tin, such as EDTA or EGTA. The system and method provide improvements over prior hydrogen peroxide disinfection systems with respect to stability, predictability and rate of reaction.

6 Claims, No Drawings

HYDROGEN PEROXIDE DISINFECTING SYSTEM FOR CONTACT LENSES

BACKGROUND OF THE INVENTION

1. Field of the Invention

The present invention relates to a system or kit for disinfecting contact lenses, and to a method of disinfecting contact lenses utilizing that kit or system. More particularly, this invention relates to a two part, hydrogen peroxide based system for disinfecting contact lenses.

2. Discussion of Related Art

Hydrogen peroxide is becoming recognized as a safe and efficacious disinfectant for contact lenses. In this regard there is unaminity between the clinicians responsible for designating such systems and the users of such products. This acceptance is primarily attributable to the fact that such systems are substantially predictable in their intended use, taking into consideration the wide range of individuals who rely upon the disinfecting effect and the good and bad habits of those individuals. However, after disinfecting, residual hydrogen peroxide must be removed before again wearing the lens. This is because hydrogen peroxide, even in trace amounts, can cause corneal irritation in sensitive individuals. It is in this respect that prior art systems fail, or introduce complications resulting in user errors, elevated costs, and unpredictability. For example, repeated rinsing to remove residual hydrogen peroxide in isotonic, buffered saline solution is effective only if repeated extractions over a longer period are made. The resulting inconvenience motivates the user to take short cuts or otherwise deviate from recommended procedure with attendant risk of imperfect removal of residual hydrogen peroxide or introduction of microorganisms. Other systems rely on enzymatic or inorganic catalysis to decompose residual hydrogen peroxide. Such systems are, when looking at the average user, problematic and slow.

The following publications provide further background concerning the use of hydrogen peroxide to disinfect contact lenses: Gasset et al., "Hydrogen Peroxide Sterilization of Hydrophilic Contact Lenses," *Archives of Ophthalmology*, Vol. 93, pages 412-415 (1975); U.S. Pat. No. 3,912,451 issued to Gaglia; and U.S. Pat. No. 4,521,375 issued to Houlsby. These publications relate to three different means for solving the same problem; namely, how to effectively neutralize the hydrogen peroxide which remains in and on a contact lens after treatment with that compound. The solutions discussed in these publications are based on the use of sodium thiosulfate (Gasset et al.), a platinum catalyst (Gaglia), and sodium pyruvate (Houlsby) to neutralize hydrogen peroxide. These systems also suffer from various problems, such as instability, unpredictability and slowness.

The present invention employs as a means to destroy residual hydrogen peroxide the well known reducing agent sodium thiosulfate. The article by Gasset et al., discloses a system which utilizes sodium thiosulfate for the same purpose, but practical difficulties relating to stability, predictability and rate of reaction have prevented the adoption of that system. The present invention provides unexpected solutions to the above-discussed prior art problems, and presents other unexpected advantages as well.

SUMMARY OF THE INVENTION

The present inventors have discovered that the problems associated with the poor stability, predictability and rate of reaction seen with the contact lens disinfection system disclosed by Gasset et al., may be overcome by utilizing sodium stannate (also known as sodium tin oxide) to stabilize the hydrogen peroxide based disinfecting solution of the present invention, more specifically the hydrogen peroxide contained in that solution. Sodium stannate is known in the chemical arts as a compound which may be utilized to stabilize hydrogen peroxide solutions. However, sodium stannate is not believed to have been used in the contact lens care art for such purpose prior to the present invention. A likely explanation for its lack of use in the lens care art is the fear of tin contamination with possible subsequent effects on the cornea.

The present inventors have discovered that such contamination and resulting possibility of damage to the cornea can be prevented by treating the lens with a neutralizing solution containing a tin complexing agent (i.e., EDTA or EGTA) and sodium thiosulfate, following treatment with a disinfecting solution containing hydrogen peroxide and sodium stannate. The tin complexing agent effectively sequesters the tin component of the sodium stannate molecule in the neutralizing solution, thereby preventing the deposition of any tin residue on the lens. The neutralizing solution also performs a second important function; namely, the sodium thiosulfate neutralizes the hydrogen peroxide remaining on the lens surface and within the lens matrix following treatment with the disinfecting solution.

In somewhat greater detail, the present invention provides a hydrogen peroxide based disinfecting system or kit, comprising two parts or components for disinfecting contact lenses; wherein the first component is presented as an aqueous solution containing hydrogen peroxide stabilized by sodium stannate, and the second component of the kit, isolated from the hydrogen peroxide component, is presented as an aqueous solution comprising sodium thiosulfate and a complexing agent capable of sequestering tin. This invention also provides a method of disinfecting contact lenses comprising first treating a contact lens to be disinfected with a hydrogen peroxide solution stabilized with sodium stannate, followed by neutralization with an aqueous solution of sodium thiosulfate comprising a complexing agent capable of sequestering tin. The compositions of the present invention, even though comprising two, distinct, separately packaged parts, may best be considered a system or kit for disinfecting contact lenses.

The contact lens disinfection system of the present invention is significantly more stable, predictable and rapid than analogous prior art systems, such as those discussed above. The improvements provided by the present invention are attributable to the unexpected synergy between the elements of the system, which synergy allows safe, convenient and rapid disinfection of contact lenses to be achieved.

DESCRIPTION OF PREFERRED EMBODIMENT

The present invention provides a two part, hydrogen peroxide based contact lens disinfection system. The two parts of the system are a disinfecting component and a neutralizing component.

The disinfecting component comprises an aqueous solution containing hydrogen peroxide and sodium stannate. The hydrogen peroxide serves to sterilize the lens, and the sodium stannate is present to stabilize the disinfecting solution, particularly the hydrogen peroxide contained therein. The disinfecting solution contains hydrogen peroxide in an amount effective to sterilize the lens. The concentration of hydrogen peroxide utilized in the disinfecting solution may vary depending on factors such as the partiular type of cleaning method utilized in the lens care regimen and the type of lenses being treated (e.g., daily wear lenses or extended wear lenses). The disinfecting solution will typically contain hydrogen peroxide at a concentration of from about 0.6% to about 6.0% by weight, preferably about 3.0% by weight, and contains sodium stannate in a concentration of from about ten parts per million to about 100 parts per million. Other ancillary agents, such as agents for pH adjustment (e.g., phosphoric acid), may be utilized in the disinfecting component, as will be appreciated by those skilled in the art. The disinfecting component does not require the use of a preservative, due to the antimicrobial action of the hydrogen peroxide contained therein.

The neutralizing component comprises an aqueous solution containing sodium thiosulate, a tin complexing agent, and preferably also a sodium thiosulfate stabilizing agent. The sodium thiosulfate is present to inactivate or neutralize any residual hydrogen peroxide present on the lens or within the lens matrix, and is contained in the neutralizing soluton in an amount effective to neutralize substantially all of the hydrogen peroxide present in and on the lens. For purposes of the present invention, substantially all of the hydrogen peroxide is considered to have been neutralized when the lens can be placed in the eye without causing stinging attributable to the presence of hydrogen peroxide in or on the lens. The amount of sodium thiosulfate contained in the neutralizing solution may vary depending on factors such as the concentration of hydrogen peroxide contained in the disinfecting solution. The neutralizing solution will typically contain sodium thiosulfate at a concentration of from about 0.5% to about 5.0% by weight, preferably about 2.5% by weight.

The tin complexing agent is selected from the group consisting of salts of ethylenediaminetetraacetic acid (EDTA) and ethyleneglycol-bis(-betaaminoethyl ether)-N,N'-tetraacetic acid (EGTA), particularly the sodium salts thereof, and is contained in the neutralizing solution in an amount effective to sequester and keep in solution the tin component of the disinfecting solution, so that the tin component can not adhere to the lens and as a result the lens will be substantially free of any tin residue on completion of the neutralization step. The amount of tin complexing agent utilized may vary depending on factors such as the amount of sodium stannate contained in the disinfecting solution. The neutralizing solution will typically contain the tin complexing agent at a concentration of from about 0.001% to about 0.05% by weight, preferably about 0.024% by weight.

The sodium thiosulfate stabilizing agent comprises one or more acids selected from the group consisting of boric acid, citric acid, maleic acid and fumaric acid, and is contained in the neutralizing solution at a concentration of from about 0.3% to about 3.0% by weight if boric acid and from about 0.1% to about 1.0% by weight if one or more of the other acids specified.

The neutralizing solution may contain other ancillary ingredients, such as sodium hydroxide for pH adjustment, as will be appreciated by those skilled in the art.

It is much preferred that the neutralizing solution be provided in units of use or "unit dose" form so that it does not require the use of a preservative, since undesirable interactions between certain preservatives and contact lenses have been experienced in the prior art. Although it is much less preferred, the solution may also be provided in a multiple use container, in which case a preservative such as polydiguanide at a concentration of from about 0.002% to about 0.02% by weight of sorbic acid at a concentration of from about 0.5% to about 5.0% by weight will be required.

In a preferred embodiment of the present invention, the disinfecting solution is presented in a master vessel and the neutralizing solution is presented in a plurality of smaller vessels to provide the two part disinfecting kit or system of the invention. In actual operation, the lens is first cleaned, rinsed with a suitable quantity of the neutralizing solution, and then placed in an appropriate vessel to which is added the disinfecting solution. After a period ranging from 1 to 20 minutes, the disinfecting solution is drained away and the vessel is refilled with the neutralizing solution. Neutralization typically occurs in from 1 to 20 minutes. At that point the lens can be removed from the vessel and installed immediately without further processing in the eye; alternatively, the lens may be stored for up to 48 hours in the neutralizing solution without repeating the disinfecting procedure.

A typical kit in accordance with the present invention will comprise the disinfecting solution contained in a master vessel having a volume on the order of 100 to 500 mL, preferably about 250 mL, and the neutralizing solution contained in a plurality of smaller vessels having individual volumes on the order of 10 to 20 ml. The volume of the master vessel and the number of smaller vessels making up a typical kit are primarily dependent on the period over which the kit is intended for use. For example, a kit which is intended for the daily disinfecting of lenses over a 30 day period would typically comprise a master vessel containing about 250 mL of the disinfecting solution and 30 smaller vessels containing 15 mL each of the neutralizing solution.

It is contemplated that the present product concept may be modified to provide kits suitable for relatively longer and shorter periods of use. It is further contemplated that the product concept may be modified to include other components in the kit, such as a cleaning component suitable for cleaning the lens prior to treatment with disinfecting solution. The abrasive cleaners described in U.S. Pat. No. 4,493,783 issued to Bhatia et al., are particularly desirable for this purpose; the entire contents of that patent are hereby incorporated by reference in the present specification to provide further description concerning the composition and used of such cleaners. One such abrasive cleaner is currently marketed under the names Opti-Clean TM and Polyclens TM.

The following example is presented to further illustrative various aspects of the present invention, and should not be interpreted as limiting the scope of the invention in any way.

EXAMPLE

The following formulations illustrate the disinfecting component and the neutralizing component of the present contact lens disinfecting system:

| Disinfecting Component | |
| --- | --- |
| Ingredient | Wt. % |
| Hydrogen Peroxide | 3.0 |
| Sodium Stannate | 0.024 |
| Phosphoric Acid | QS pH 3 |
| Purified Water | QS 100 mL |

The disinfecting component is prepared by filtering the purified water through a 0.2 micron water filter. The hydrogen peroxide is then added to the purified water with stirring. After approximately 20 minutes of continuous stirring, the sodium stannate is added with stirring, and the resulting mixture is stirred for an additional 20 minutes. The pH of the resulting solution is then adjusted to pH 3 using phosphoric acid.

| Neutralizing Component | |
| --- | --- |
| Ingredient | Wt. % |
| Sodium Thiosulfate | 2.5 |
| EDTA | 0.015 |
| Boric Acid | 0.6 |
| 1N NaOH | QS pH 7 |
| Purified Water | QS 100 mL |

The neutralizing component is prepared by sequentially dissolving the sodium thiosulfate and the EDTA in a portion of the purified water with stirring to form a first solution. A second solution is then prepared by heating a portion of the water to about 40° C. and dissolving the boric acid therein. The first and second solutions are then combined, and the pH of the resulting solution is adjusted to pH 7 using NaOH.

The present invention has been described above in connection with certain preferred embodiments. However, as obvious variations thereon will become apparent to those skilled in the art, the invention is not to be considered as limited thereto.

What is claimed is:

1. A method of disinfecting a contact lens, comprising:

soaking the lens in an aqueous sterilizing solution containing an amount of hydrogen peroxide effective to sterilize the lens and a hydrogen peroxide stabilizing agent, said stabilizing agent consisting essentially of sodium stannate at a concentration of about 10 to 100 parts per million, thereby sterilizing the lens; and contacting the sterilized lens with an aqueous neutralizing solution containing an amount of sodium thiosulfate effective to neutralize substantially all of the hydrogen peroxide present in and on the lens following treatment with the disinfecting solution and an amount of a tin complexing agent effective to sequester substantially all of the tin introduced into the neutralizing solution by the sterilized lens, said neutralizing solution having a pH of about 7.

2. A method of disinfecting contact lenses according to claim 1, wherein the tin complexing agent is selected from the group consisting of EDTA, EGTA, and combinations thereof.

3. A method of disinfecting contact lenses according to claim 2, wherein the disinfecting solution contains from about 0.6 to 6.0 wt.% hydrogen peroxide; and the neutralizing solution contains from about 0.5 to about 5.0 wt.% sodium thiosulfate, and from about 0.001 to about 0.05 wt.% of the tin complexing agent.

4. A method of disinfecting contact lenses according to claim 3, wherein the neutralizing solution further comprises an effective amount of a sodium thiosulfate stabilizing agent selected from the group consisting of boric acid, citric acid, maleic acid and fumaric acid.

5. A method of cleaning contact lenses according to claim 4, wherein the sodium thiosulfate stabilizing agent comprises boric acid in an amount of from about 0.3 to about 3.0 wt.%.

6. A method of cleaning contact lenses according to claim 4, wherein the sodium thiosulfate stabilizing agent is selected from the group consisting of citric acid, maleic acid and fumaric acid, and is contained in the neutralizing solution in an amount of from about 0.1 to about 1.0 wt.%.

* * * * *